US012807562B2

(12) United States Patent
Ha et al.

(10) Patent No.: US 12,807,562 B2
(45) Date of Patent: Nov. 24, 2026

(54) DIAMINE COMPOUND HAVING LOW HYGROSCOPICITY AND LOW DIELECTRIC CONSTANT, ITS POLYMER, AND POLYIMIDE FILM USING THE POLYMER

(71) Applicant: PUSAN NATIONAL UNIVERSITY INDUSTRY-UNIVERSITY COOPERATION FOUNDATION, Busan (KR)

(72) Inventors: Chang Sik Ha, Busan (KR); Jun Seok Lee, Busan (KR); Sung Soo Park, Busan (KR); Amol Maruti Jadhav, Busan (KR); Yong Zhu Yan, Busan (KR)

(73) Assignee: PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 497 days.

(21) Appl. No.: 18/477,758

(22) Filed: Sep. 29, 2023

(65) Prior Publication Data

US 2024/0199532 A1 Jun. 20, 2024

(30) Foreign Application Priority Data

Sep. 30, 2022 (KR) ........................ 10-2022-0125434
Jan. 4, 2023 (KR) ........................ 10-2023-0001089

(51) Int. Cl.

*C07C 229/60* (2006.01)
*C08G 73/10* (2006.01)
*C08J 5/18* (2006.01)

(52) U.S. Cl.

CPC ........ *C07C 229/60* (2013.01); *C08G 73/1039* (2013.01); *C08G 73/1067* (2013.01); *C08J 5/18* (2013.01); *C08J 2479/08* (2013.01)

(58) Field of Classification Search

CPC .................................................... C07C 229/60
See application file for complete search history.

(56) References Cited

U.S. PATENT DOCUMENTS 8,828,476 B2 * 9/2014 Ha .......................... C08K 9/00
977/932
2021/0179819 A1 * 6/2021 Belin ........................ C08L 7/00
2024/0279156 A1 * 8/2024 Ha ........................ C07C 217/86

FOREIGN PATENT DOCUMENTS

KR 2020-0042222 4/2020

OTHER PUBLICATIONS

IUPAC, Compendium of Chemical Terminology, Gold Book, pp. 21-22 ("acid anhydride") (2014) (Year: 2014).*
J. Lee et al., 14 Polymers, 1-17 (2022) (Year: 2022).*

* cited by examiner

*Primary Examiner* — Alexander R Pagano
(74) *Attorney, Agent, or Firm* — NORTON ROSE FULBRIGHT US LLP

(57) ABSTRACT

Disclosed are a novel diamine compound, a polyimide precursor produced using the same, polyimide produced from the polyimide precursor, and a polyimide film manufactured using the polyimide. The novel diamine compound is represented by a following Chemical Formula 1:

[Chemical Formula 1]

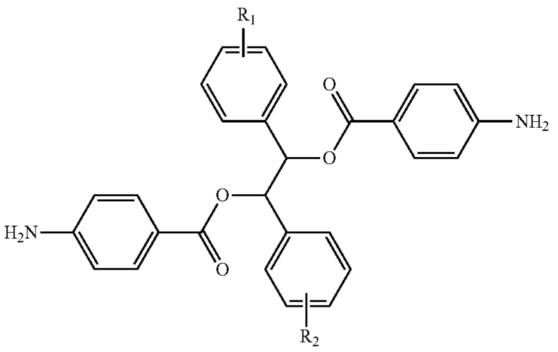

where in the Chemical Formula 1, each of $R_1$ and $R_2$ independently represents hydrogen, an alkyl group having 1 to 5 carbon atoms, or a trifluoromethyl group.

9 Claims, 14 Drawing Sheets

GPC Results

| | Dist Name | Mn | Mw | Mv | MP | Mz | Mz+1 | Polydispersity | K | alpha | % Area |
|---|---|---|---|---|---|---|---|---|---|---|---|
| 1 | | 10596 | 23273 | | 19982 | 40832 | 61995 | 2.196265 | | | 100.00 |

DIAMINE COMPOUND HAVING LOW HYGROSCOPICITY AND LOW DIELECTRIC CONSTANT, ITS POLYMER, AND POLYIMIDE FILM USING THE POLYMER

CROSS-REFERENCE TO RELATED APPLICATION

This application claims priority from Korean Patent Application No. 10-2022-0125434 (2022.09.30) filed on Sep. 30, 2022 and Korean Patent Application No. 10-2023-0001089 on Jan. 4, 2023 in the Korean Intellectual Property Office, and all the benefits accruing therefrom under 35 U.S.C. 119, the contents of which in its entirety are herein incorporated by reference.

BACKGROUND

Field

The present disclosure relates to a novel diamine compound, a polyimide precursor produced using the same, polyimide produced from the polyimide precursor, and a polyimide film manufactured using the polyimide.

Description of Related Art

As wireless communication technology develops rapidly, various demands for big data, an automotive, and a mobile phone using 5G and 6G wireless communications using a high frequency broadband are rapidly increasing. In the 5G and 6G wireless communications using the high-frequency broadband, a signal transmission speed, prevention of signal distortion due to dielectric loss, and signal integrity are important. To achieve those important factors, a material with a low dielectric constant and low dielectric loss at high frequencies should be used in electronic devices.

In order to meet this need, polymers such as polyimide, polyphenylene ether, benzocyclobutene resins, polysilsesquioxane, polybenzimidazole, polybutylene terephthalate, fluoropolymers, and polynaphthalene are being actively researched. Among them, polyimide not only exhibits excellent heat resistance and mechanical properties, but also has excellent chemical resistance and appropriate dielectric properties. Thus, polyimide is known as a material that may be applied to industries such as next-generation wireless communications and electronic devices.

The polyimide may be used to produce a film for use as a substrate. However, there is a problem in that polyimide does not have high solubility in a polar solvent, making it difficult to convert the polyimide into a film. Furthermore, polyimide is required to have a low dielectric constant. However, a conventional polyimide film has a problem of having a rather high dielectric constant.

Therefore, research is needed to produce polyimide with desirable dielectric properties in a wide range of high frequencies.

SUMMARY

A purpose of the present disclosure is to provide a novel diamine compound that has high transparency and heat resistance while also having low water absorption and a low dielectric constant, a polyimide precursor produced using the same, polyimide produced from the polyimide precursor, and a polyimide film manufactured using the polyimide.

Purposes according to the present disclosure are not limited to the above-mentioned purpose. Other purposes and advantages according to the present disclosure that are not mentioned may be understood based on following descriptions, and may be more clearly understood based on embodiments according to the present disclosure. Further, it will be easily understood that the purposes and advantages according to the present disclosure may be realized using means illustrated in the claims and combinations thereof.

One aspect of the present disclosure provides a diamine compound represented by a following Chemical Formula 1:

[Chemical Formula 1]

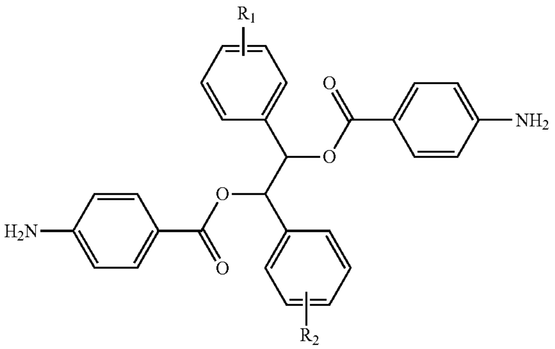

where in the Chemical Formula 1, each of $R_1$ and $R_2$ independently represents hydrogen, an alkyl group having 1 to 5 carbon atoms, or a trifluoromethyl group.

In one implementation, the diamine compound is represented by a following Chemical Formula 1-1:

[Chemical Formula 1-1]

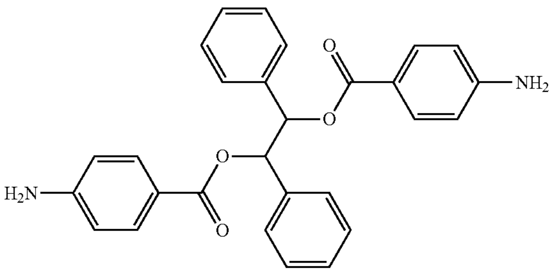

Another aspect of the present disclosure provides a polyimide precursor produced by polymerizing of a polymerization component containing at least one acid dianhydride and the diamine compound.

In one implementation, the acid dianhydride is 6-FDA (4,4'-(hexafluoroisopropylidene)diphthalic anhydride).

Another aspect of the present disclosure provides polyimide produced from the polyimide precursor.

In one implementation, the polyimide is represented by a following Chemical Formula 2:

[Chemical Formula 2]

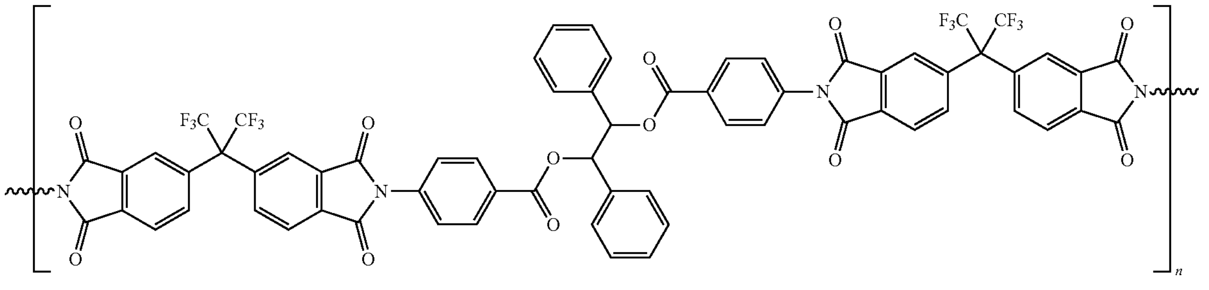

where in the Chemical Formula 2, n is an integer from 8 to 75.

In one implementation, the polyimide is soluble in a polar solvent selected from a group consisting of dimethyl sulfoxide (DMSO), dimethylacetamide (DMAc), tetrahydrofuran (THF), chloroform ($CHCl_3$), dichloromethane ($CH_2Cl_2$), ethyl acetate, and γ-butylrolactone at a temperature of 10 to 40° C.

In one implementation, a weight average molecular weight (Mw) of the polyimide is in a range of 20,000 to 25,000.

Still another aspect of the present disclosure provides a polyimide film manufactured by dissolving the polyimide according to claim 6 in a polar solvent at a temperature of 10 to 40° C. to produce a solution, and applying the produced solution on a substrate, and then drying the applied solution.

In one implementation, the polar solvent is selected from a group consisting of dimethyl sulfoxide (DMSO), dimethylacetamide (DMAc), tetrahydrofuran (THF), chloroform ($CHCl_3$), dichloromethane ($CH_2Cl_2$), ethyl acetate, and γ-butylrolactone.

The novel diamine compound represented by the Chemical Formula 1 includes an ester group and a phenyl group. When the diamine compound of the present disclosure which has the above structure is used to produce a polymer, that is, polyimide, the diamine compound may reduce an imide group content in a polymer main chain and increase a space between polymer chains to effectively lower the dielectric constant of the polymer. Furthermore, the space between the polymer chains is increased, such that a solvent molecule easily penetrates into the polymer, and thus a solubility of the polyimide as the polymer may be improved. In addition, a charge transfer complex unique to polyimide may be suppressed such that the polyimide may be colorless and transparent.

In other words, the polyimide film manufactured using the novel diamine compound according to the present disclosure has high transparency and heat resistance while also having low water absorption and a low dielectric constant, and thus has high applicability to industries such as next-generation wireless communications and electronic devices.

Effects of the present disclosure are not limited to the above-mentioned effects, and other effects as not mentioned will be clearly understood by those skilled in the art from following descriptions.

DETAILED DESCRIPTIONS

Figure 1:
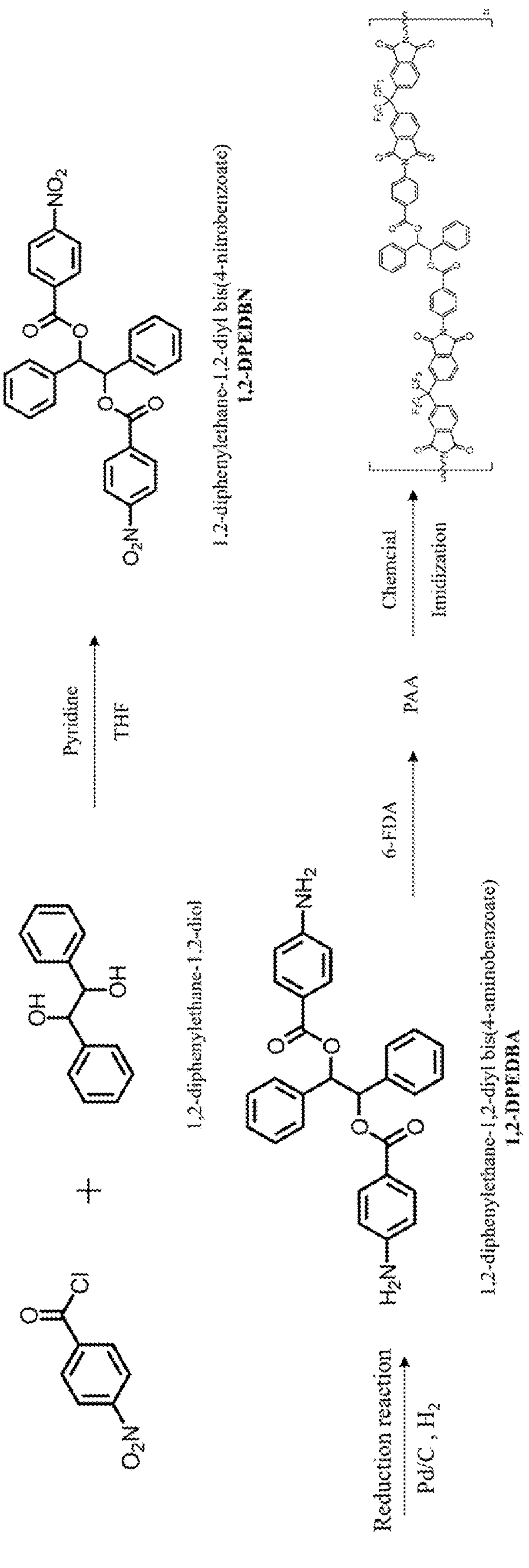
FIG. 1 is a schematic diagram showing a synthesis process of a novel diamine compound, and a producing process of polyimide therefrom, according to an embodiment of the present disclosure.

Advantages and features of the present disclosure, and a method of achieving the advantages and features will become apparent with reference to embodiments described later in detail together with the accompanying drawings. However, the present disclosure is not limited to the embodiments as disclosed below, but may be implemented in various different forms. Thus, these embodiments are set forth only to make the present disclosure complete, and to completely inform the scope of the present disclosure to those of ordinary skill in the technical field to which the present disclosure belongs, and the present disclosure is only defined by the scope of the claims.

Further, descriptions and details of well-known steps and elements are omitted for simplicity of the description. Furthermore, in the following detailed description of the present disclosure, numerous specific details are set forth in order to provide a thorough understanding of the present disclosure.

However, it will be understood that the present disclosure may be practiced without these specific details. In other instances, well-known methods, procedures, components, and circuits have not been described in detail so as not to unnecessarily obscure aspects of the present disclosure. Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is directed to the purpose of describing particular embodiments only and is not intended to be limiting of the present disclosure. As used herein, the singular constitutes "a" and "an" are intended to include the plural constitutes as well, unless the context clearly indicates otherwise. It will be further understood that the terms "comprise", "comprising", "include", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of associated listed items. Expression such as "at least one of" when preceding a list of elements may modify the entire list of elements and may not modify the individual elements of the list. In interpretation of numerical values, an error or tolerance therein may occur even when there is no explicit description thereof.

In descriptions of temporal relationships, for example, temporal precedent relationships between two events such as "after", "subsequent to", "before", etc., another event may occur therebetween unless "directly after", "directly subsequent" or "directly before" is not indicated.

When a certain embodiment may be implemented differently, a function or an operation specified in a specific block may occur in a different order from an order specified in a flowchart. For example, two blocks in succession may be actually performed substantially concurrently, or the two blocks may be performed in a reverse order depending on a function or operation involved.

The features of the various embodiments of the present disclosure may be partially or entirely combined with each other, and may be technically associated with each other or operate with each other. The embodiments may be implemented independently of each other and may be implemented together in an association relationship.

In interpreting a numerical value, the value is interpreted as including an error range unless there is no separate explicit description thereof.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, "embodiments," "examples," "aspects, and the like should not be construed such that any aspect or design as described is superior to or advantageous over other aspects or designs.

Further, the term 'or' means 'inclusive or' rather than 'exclusive or'. That is, unless otherwise stated or clear from the context, the expression that 'x uses a or b' means any one of natural inclusive permutations.

The terms used in the description below have been selected as being general and universal in the related technical field. However, there may be other terms than the terms depending on the development and/or change of technology, convention, preference of technicians, etc. Therefore, the terms used in the description below should not be understood as limiting technical ideas, but should be understood as examples of the terms for describing embodiments.

FIG. 1 is a schematic diagram showing a synthesis process of a novel diamine compound, and a producing process of polyimide therefrom, according to an embodiment of the present disclosure.

Referring to FIG. 1, a diamine compound according to an embodiment of the present disclosure may be represented by a following Chemical Formula 1:

[Chemical Formula 1]

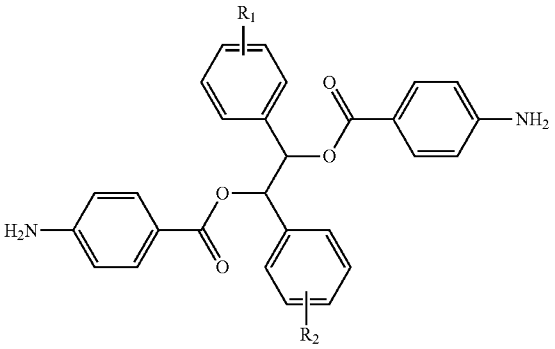

In the Chemical Formula 1, each of $R_1$ and $R_2$ independently represents hydrogen, an alkyl group having 1 to 5 carbon atoms, or a trifluoromethyl group.

In one embodiment, the diamine compound may be represented by a following Chemical Formula 1-1:

[Chemical Formula 1-1]

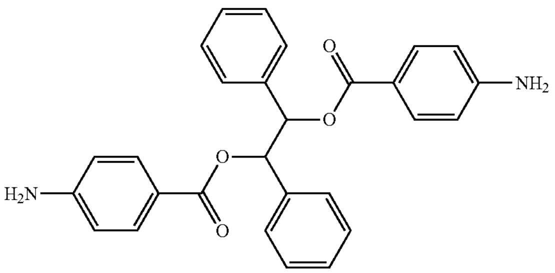

The novel diamine compound represented by the Chemical Formula 1 includes an ester group and a phenyl group. When the diamine compound of the present disclosure which has the above structure is used to produce a polymer, that is, polyimide, the diamine compound may reduce an imide group content in a polymer main chain and increase a space between polymer chains to effectively lower the dielectric constant of the polymer. Furthermore, the space between the polymer chains is increased, such that a solvent molecule easily penetrates into the polymer, and thus a solubility of the polyimide as the polymer may be improved.

In addition, a charge transfer complex unique to polyimide may be suppressed such that the polyimide may be colorless and transparent.

In one embodiment, as shown in FIG. 1, the novel diamine compound of the present disclosure may be synthesized by synthesizing a dinitro compound via a condensation reaction of 4-nitrobenzoyl chloride and 1,2-diphenylethane-1,2-diol, and then by performing a reduction reaction on the dinitro compound using a palladium/carbon catalyst and hydrogen gas.

In one embodiment, a polyimide precursor may be synthesized via condensation polymerization of a polymerization component containing one or more acid dianhydrides and the novel diamine compound of the present disclosure. More specifically, the diamine compound may be polymerized with 6-FDA (4,4'-(hexafluoroisopropylidene)diphthalic anhydride) to synthesize the polyimide precursor polymer having a sufficient number average molecular weight of about 10,000.

In one example, the polyimide may be synthesized via a chemical imidization process of the polyimide precursor.

Further, a polyimide film may be produced by dissolving the polyimide in a polar solvent at a temperature of 10 to 40° C. to produce a solution, and applying the produced solution on a substrate, and then drying the same.

In one embodiment, the polyimide may be represented by a following Chemical Formula 2 and may have a weight average molecular weight (Mw) of 20,000 to 25,000:

In one example, the polyimide film had a 5 weight percent (wt %) loss temperature of about 360° C. and thus exhibited high heat resistance. Furthermore, a water contact angle was 90.26° on average, thus indicating hydrophobic properties. A moisture absorption percentage thereof after immersion thereof in water for 24 hours was 1.78%, and thus had excellent moisture barrier properties.

In addition, the polyimide film manufactured in accordance with the present disclosure exhibits a transmittance of 87.1% in a visible light region, and thus, high transparency. A dielectric constant thereof is 1.87 at $10^7$ Hz. Thus, the polyimide film manufactured in accordance with the present disclosure exhibited significantly better performance compared to commercially available polyimide (3.3) and other polyimides based on 6-FDA.

In other words, the polyimide film manufactured using the novel diamine compound according to the present disclosure has high transparency and heat resistance while also having low water absorption and the low dielectric constant, and thus has high applicability to industries such as next-generation wireless communications and electronic devices.

Hereinafter, examples of the present disclosure are described in detail. However, the examples as described below are only some embodiments of the present disclosure, and the scope of the present disclosure is not limited to the examples below.

[Chemical Formula 2]

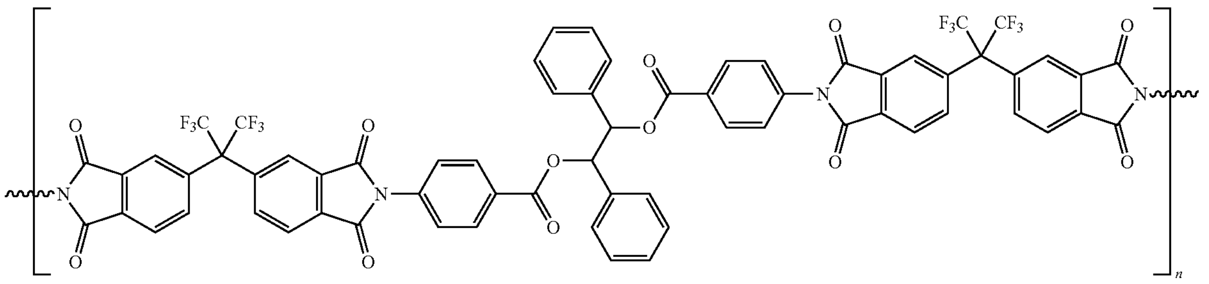

In the Chemical Formula 2, n is an integer from 8 to 75.

The polyimide produced in accordance with the present disclosure may be soluble in a polar organic solvent with a high boiling point such as dimethylacetamide (N,N'-dimethylacetamide) or dimethyl sulfoxide (DMSO) at room temperature, and may be easily soluble in a polar solvent with a low boiling point such as chloroform, dichloromethane, and tetrahydrofuran (THF), and thus exhibits excellent solubility compared to other commercially available polyimides. Furthermore, the polyimide produced in accordance with the present disclosure may have excellent solubility in ethyl acetate and may also be dissolved in gamma butyrolactone (γ-butylrolactone) at room temperature.

This is because in the polyimide produced in accordance with the present disclosure, a bulky phenyl group is introduced to the polymer main chain, increasing a free volume between polymer chains, and thus allowing a solvent molecule to easily penetrate into a space between molecules. Therefore, the polyimide produced in accordance with the present disclosure has excellent solubility in a larger number of types of solvents than conventional polyimide has, and thus may be easily converted to a film.

In one example, the polyimide film according to the present disclosure may exhibit excellent performance.

Example 1

Synthesis of 1,2-diphenylethane-1,2-diol

We added 5.0 g of benzoin and 80 ml of methanol to a 250 ml round flask and stirred a mixed solution for 30 minutes, then slowly added 1.3 g of sodium borohydride thereto, followed by stirring thereof for 2 hours. After the stirring, 50 ml of distilled water was added thereto, and an organic layer was separated therefrom using a separatory funnel, and then was concentrated using a rotary concentrator to obtain a powder substance, which in turn was then dried in an oven at 80° C. for 15 hours to produce a final substance 1,2-diphenylethane-1,2-diol.

Example 2

Synthesis of 1,2-diphenylethane-1,2-diylbis(4-nitrobenzoate) (1,2-DPEDBN)

5.0 g of 1,2-diphenylethane-1,2-diol and 25 ml of anhydrous tetrahydrofuran were added to a 500 ml round flask which was sealed under a nitrogen atmosphere. Afterwards, 8.65 g of 4-nitrobenzoyl chloride and 25 ml of a solvent were added to the flask under a condition of 0° C. Thereafter, 11.29 ml of pyridine was slowly added thereto. The mixed solution was stirred for 24 hours, then and a powder substance was obtained through a vacuum filter, and dried in an oven at 80° C. for 15 hours to produce a final substance 1,2-diphenylethane-1,2-diylbis(4-nitrobenzoate).

Example 3

Producing 1,2-diphenylethane-1,2-diylbis(4-aminobenzoate) (1,2-DPEDBA)

5.0 g of 1,2-DPEDBN, 0.5 g of palladium/carbon catalyst, and 120 ml of dehydrated tetrahydrofuran were added to a 250 ml round flask under a nitrogen atmosphere, followed by stirring for 30 minutes. Thereafter, three balloons containing hydrogen gas therein were inserted into the round flask to apply a sufficient pressure thereto. After stirring the mixed solution for 24 hours, the catalyst in the mixed solution was separated therefrom using Celite 525, and the mixed solution free of the catalyst was concentrated using a rotary concentrator and then recrystallized with n-hexane. Thus, powders were obtained. Afterwards, the powders were dried in a vacuum oven at 80° C. for 15 hours to obtain a final substance 1,2-diphenylethane-1,2-diylbis(4-aminobenzoate).

Example 4

Producing Polyamic Acid and Polyimide Powder

Polyamic acid as a precursor to polyimide is formed via the condensation polymerization reaction of diamine and dianhydride. In a 20 ml vial, 2.0 mmol 1,2-diphenylethane-1,2-diylbis(4-aminobenzoate) (933 mg), 2.0 mmol 4,4'-(hexafluoroisopropylidene)diphthalic anhydride were dissolved in a dimethylacetamide solvent at a solid content of 25 wt % under a nitrogen atmosphere, followed by stirring at 0° C. for 2 hours, and then stirring at room temperature for 72 hours. Afterwards, for the chemical imidization process, 0.81 ml of pyridine and 1.89 ml of acetic anhydride were added thereto, followed by stirring for 24 hours under a nitrogen atmosphere. The stirred solution was slowly poured into 200 ml of methanol/distilled water 1:1 mixed solution to produce a precipitate. The precipitate was washed with methanol and distilled water, filtered, and dried in a vacuum oven at 80° C. for 15 hours to obtain polyimide powders (6-FDA-DPEDBA).

Example 5

Manufacturing Polyimide Film

In a 10 ml vial, 0.35 g of polyimide powder (6-FDA-DPEDBA) was dissolved in 2.78 mL of γ-butylrolactone at a solid content of 10 wt % to prepare a solution, and then the solution was subjected stirring until the solution was transparent and homogeneous. Afterwards, 1.2 ml of the solution was applied to a glass substrate and dried at 80° C. for 24 hours under a nitrogen atmosphere to manufacture a polyimide film.

COMPARATIVE EXAMPLE

Poly(pyromellitic dianhydride-co-4,4'-oxydianiline) (PMDA-ODA PI) was synthesized. The polyamic acid (PAA) solution was produced by polymerization and thermal imidization of diamine (ODA) and dianhydride (PMDA).

First, ODA (2.0 mmol) and PMDA (2.0 mmol) at an equimolar amount were added to 7.1 mL of DMAc to prepare a solution. After stirring the solution for 24 hours under a nitrogen atmosphere at room temperature, PAA was applied to a glass slide using a dropper and dried at 60° C. under a nitrogen atmosphere overnight.

Next, the film was thermally imidized at a heating rate of 1° C./min, at 80° C. for 2 hours, at 120° C. for 1 hour, at 180° C. for 1 hour, at 250° C. for 0.5 hour, and at 300° C. for 0.5 hour. Afterwards, the slide glass was immersed in deionized water to obtain a final polyimide film.

Experimental Example 1

Whether each of 1,2-diphenylethane-1,2-diol (1,2-DPEDBN) as the precursor of the novel diamine according to the present disclosure and 1,2-DPEDBA as the novel diamine was successfully synthesized was identified via nuclear magnetic resonance analysis.

Figure 2:
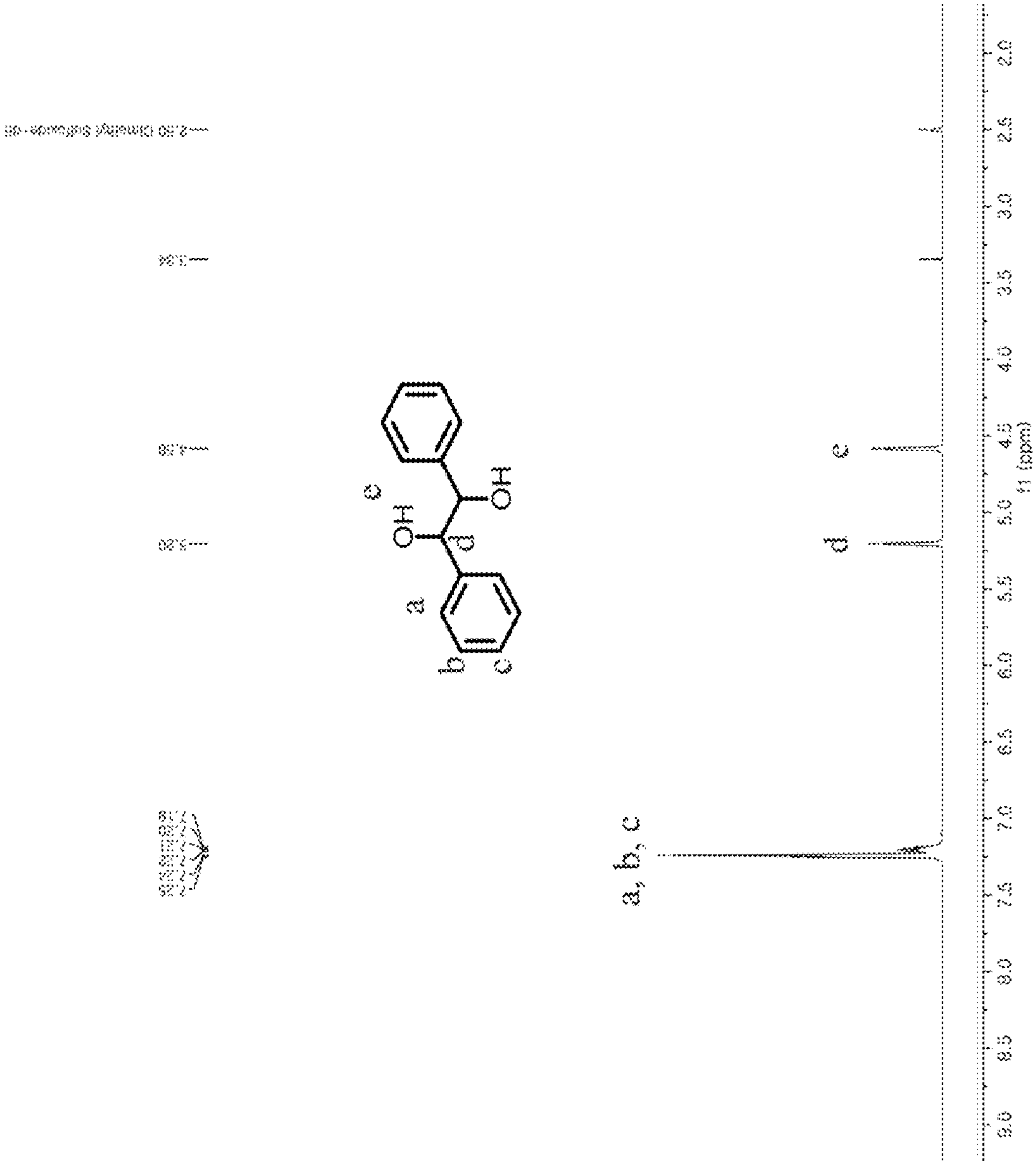
FIG. 2 to FIG. 6 show proton nuclear magnetic resonance spectra of substances synthesized according to an embodiment of the present disclosure, respectively.

The proton nuclear magnetic resonance spectrum of 1,2-diphenylethane-1,2-diol as shown in FIG. 2 exhibited peaks at 7.25, 7.24, 7.21, 5.20, and 4.55 ppm. In this regard, the peaks appearing at 7.25 to 7.21 ppm are due to hydrogen in the phenyl group, the peak appearing at 5.20 ppm is due to the —CH group, and the peak appearing at 4.55 ppm is due to the —OH group.

Figure 3:
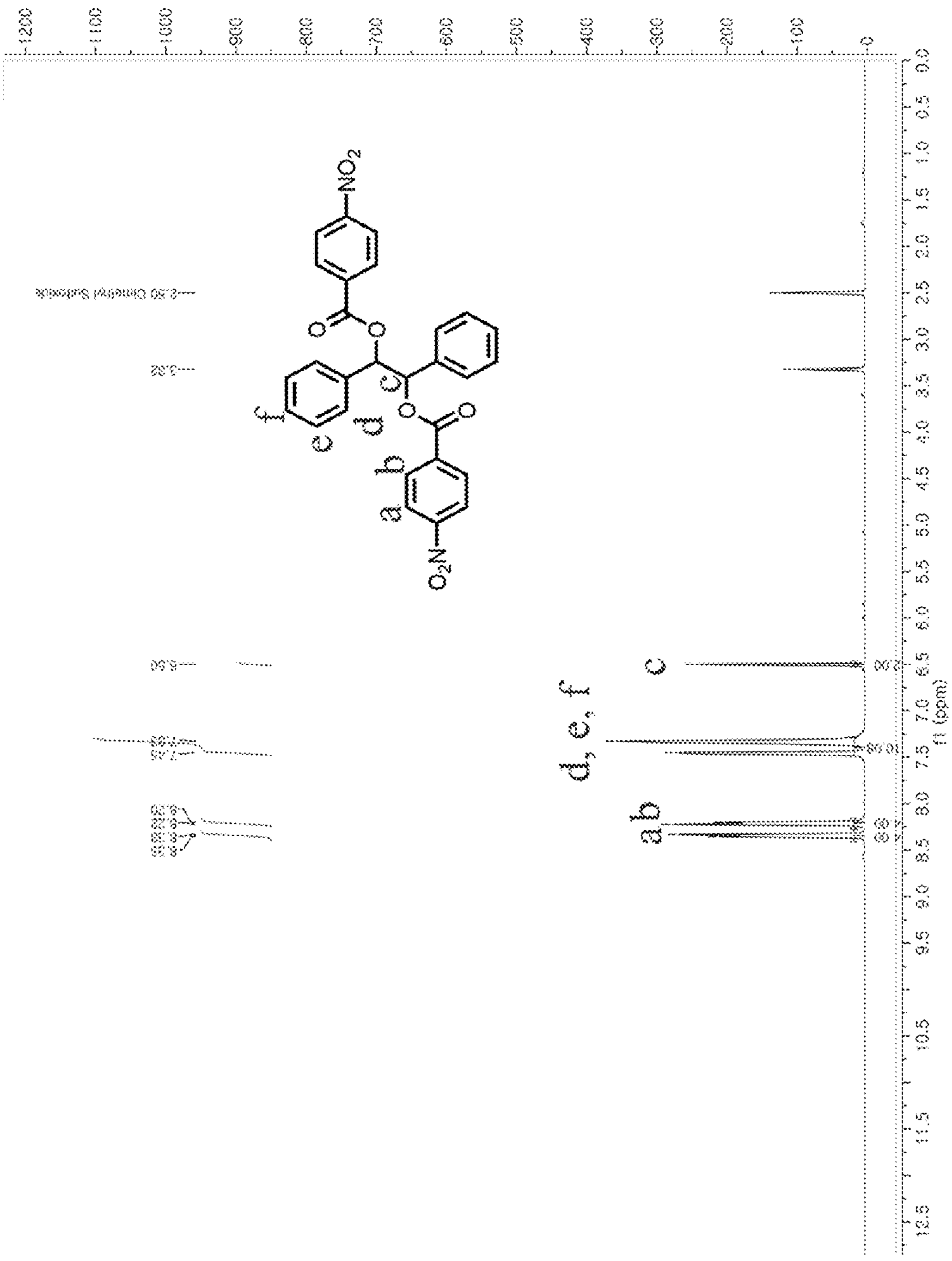

The proton nuclear magnetic resonance spectrum of 1,2-DPEDBN as shown in FIG. 3 exhibited peaks at 8.33, 8.32, 7.45, 7.33, and 6.50 ppm. The peaks appearing at 8.33 and 8.32 ppm are due to the hydrogen of the benzene ring to which the nitro group is attached, the peaks appearing at 7.45 and 7.33 ppm are due to the hydrogen in the phenyl group, and the peak appearing at 6.50 ppm is due to the —CH group.

Figure 4:
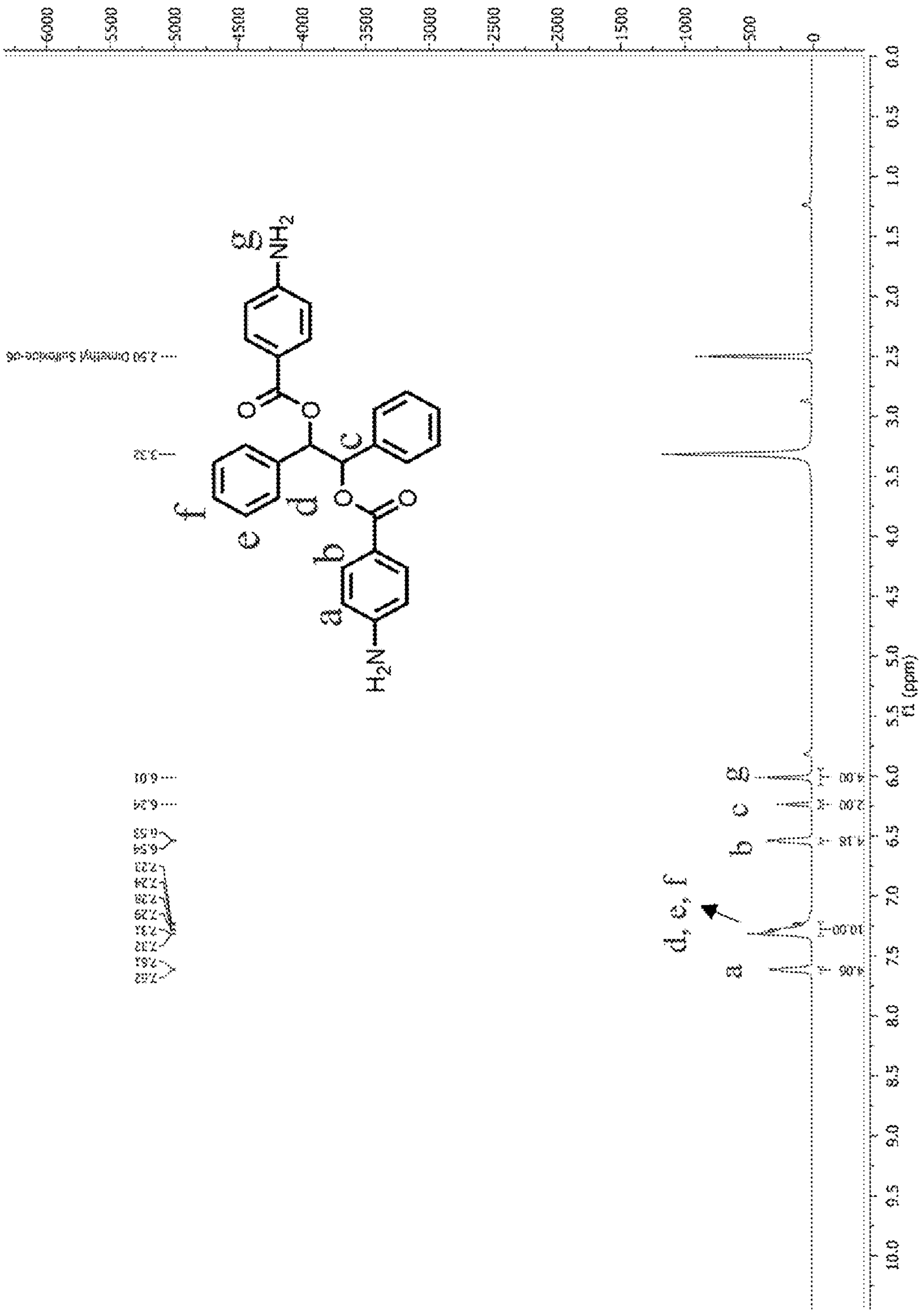

The 1,2-DPEDBA proton nuclear magnetic resonance spectrum as shown in FIG. 4 exhibited peaks at 7.62, 7.29, 6.54, 6.24, and 6.01 ppm. The peaks at 7.62 and 6.54 ppm are due to the hydrogen of the benzene ring to which an amine group is attached. The peaks appearing at around 7.29 ppm are due to hydrogen in the phenyl group, the peak appearing at 6.24 ppm is due to the —CH group, and the peak appearing at 6.01 ppm is due to the —$NH_2$ group.

Figure 5:
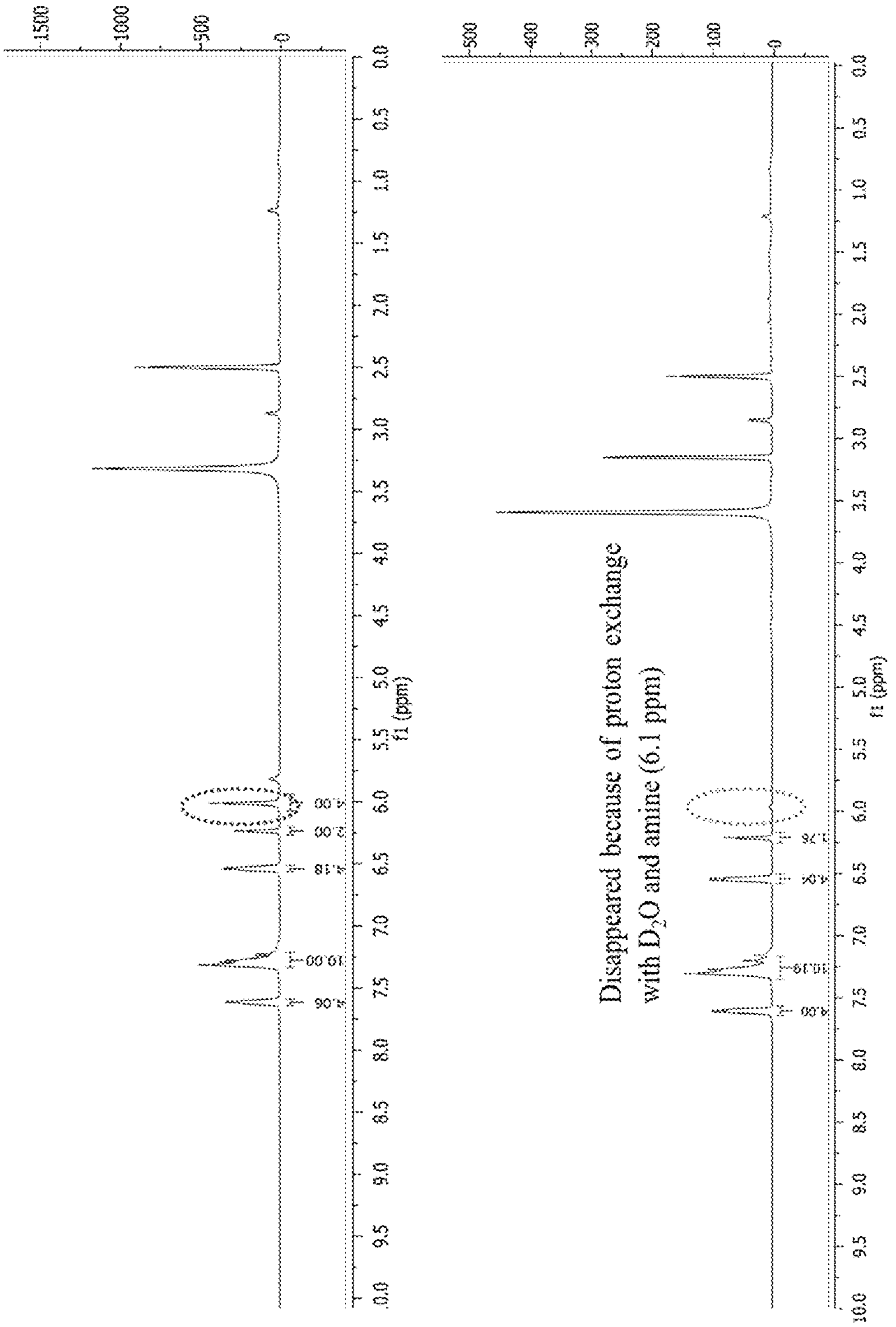

Furthermore, the proton nuclear magnetic resonance spectrum as shown in FIG. 5 is about a product obtained by adding $D_2O$ to 1,2-DPEDBA. When FIG. 5 is compared to FIG. 4, the —$NH_2$ peak at 6.01 ppm disappears. Thus, it is identified that the peak at 6.01 ppm is due to the hydrogen of the —$NH_2$ group.

Figure 6:
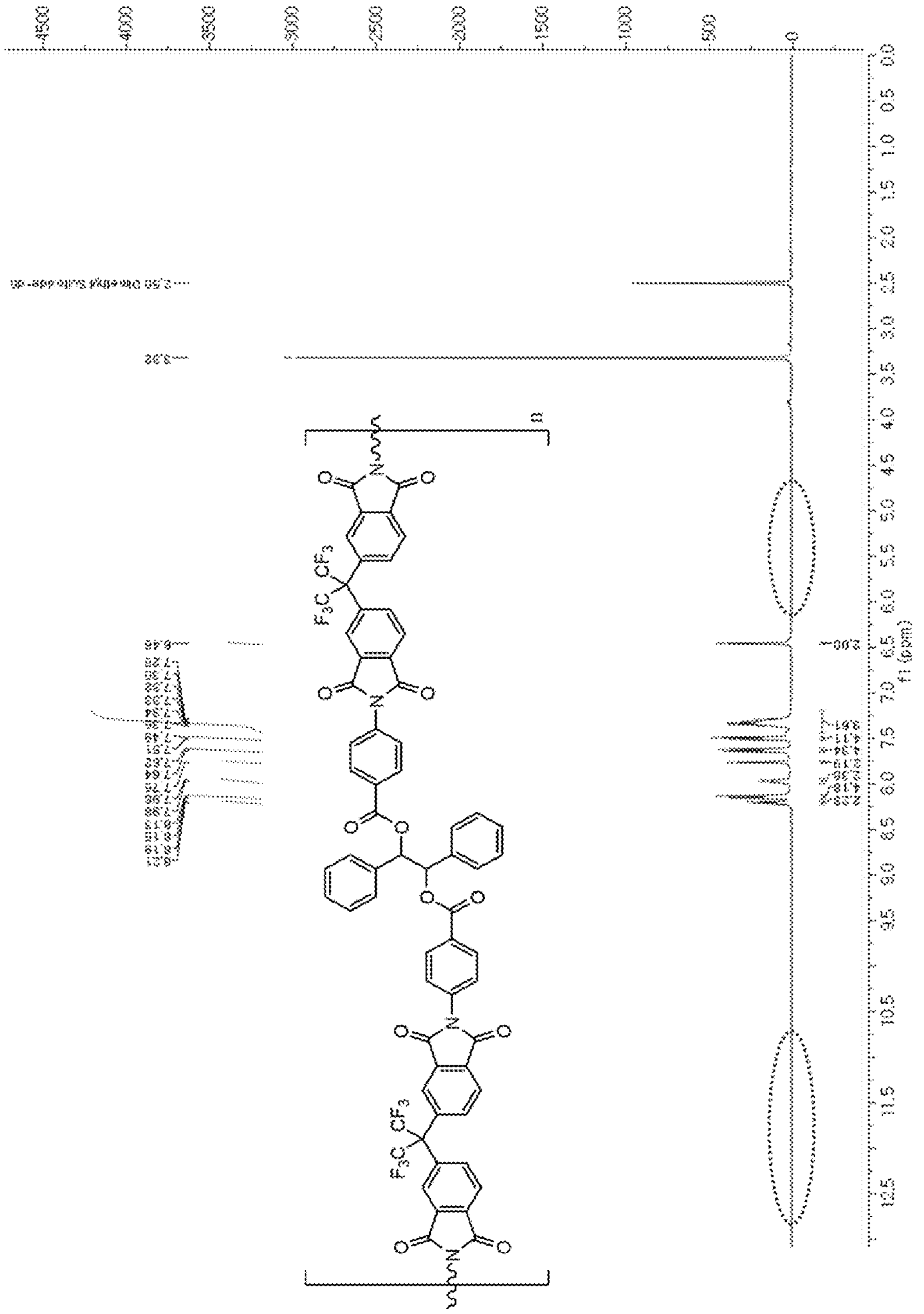

The proton nuclear magnetic resonance spectrum as shown in FIG. 6 is about solid polyimide that has gone through a chemical imidization process. In FIG. 6, peaks are absent at 12 ppm and 5 to 6 ppm. Thus, it may be identified that —COOH and —NH of the polyamic acid as the polyimide precursor do not exist, and thus that the polyimide was successfully synthesized.

Based on the proton nuclear magnetic resonance spectra in FIGS. 2 to 6, it was identified that the substances as produced in the examples were successfully synthesized.

Experimental Example 2

Whether each of 1,2-DPEDBN as a novel monomer precursor, 1,2-DPEDBA as a novel diamine monomer, and polyimide as produced in accordance with the present disclosure was successfully synthesized was identified via through functional group analysis.

Figure 7:
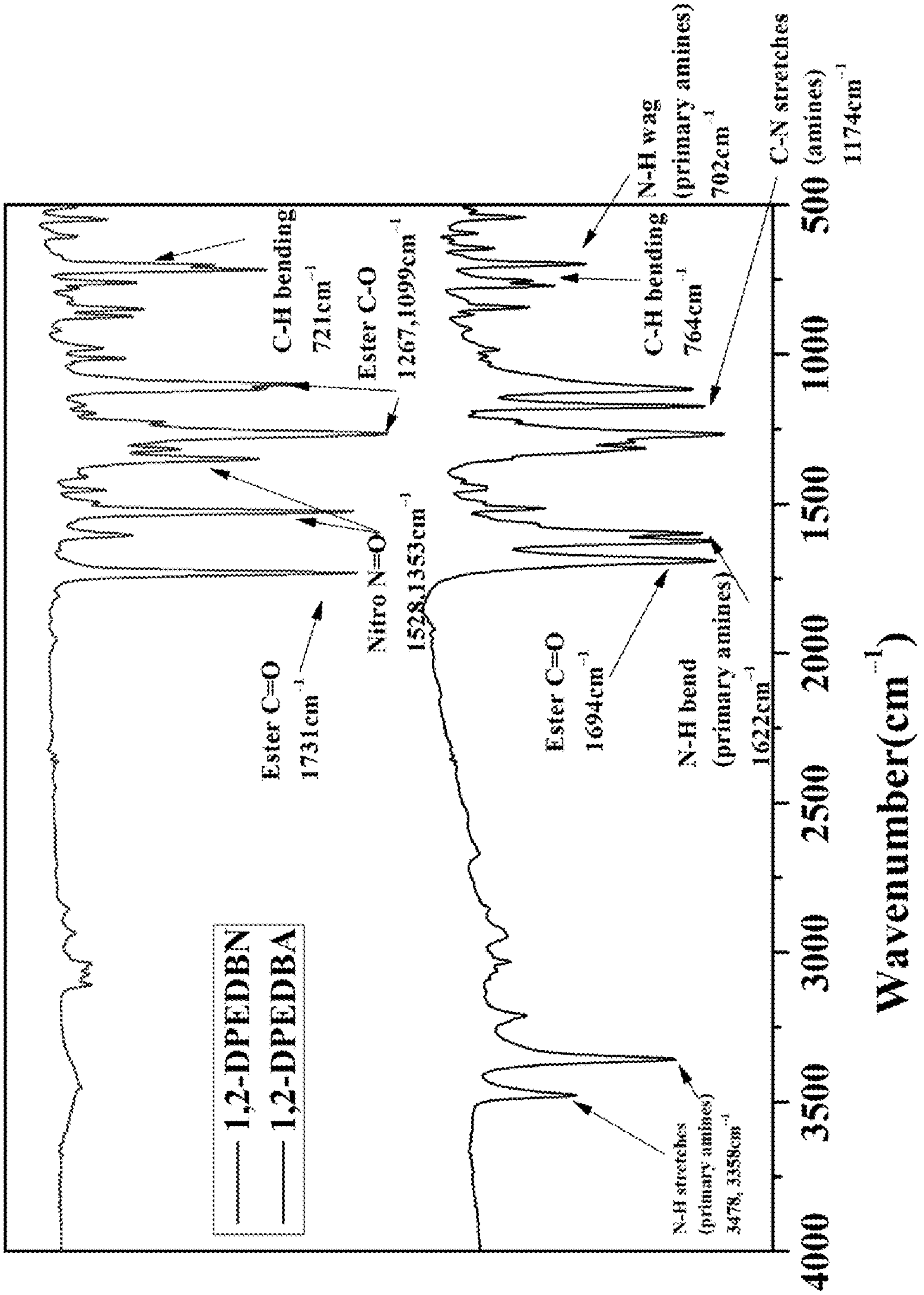
FIG. 7 shows a FT-IR spectrum of each of 1,2-diphenylethane-1,2-diylbis(4-nitrobenzoate and 1,2-diphenylethane-1,2-diylbis(4-aminobenzoate) synthesized according to an embodiment of the present disclosure.

The FT-IR spectrum of 1,2-DPEDBN (red line) as shown in FIG. 7 exhibits peaks at 1731, 1267, and 1099 $cm^{-1}$, which are due to the —C═O and —C—O groups of the ester group. Furthermore, the peaks appearing at 1528 and 1353 cm−1 are due to the nitro group. On the other hand, the FT-IR spectrum of 1,2-DPEDBA (black line) exhibits peaks at 3478, 3358, 1622, 1174, and 702 $cm^{-1}$, thus indicating the presence of a —$NH_2$ group.

Figure 8:
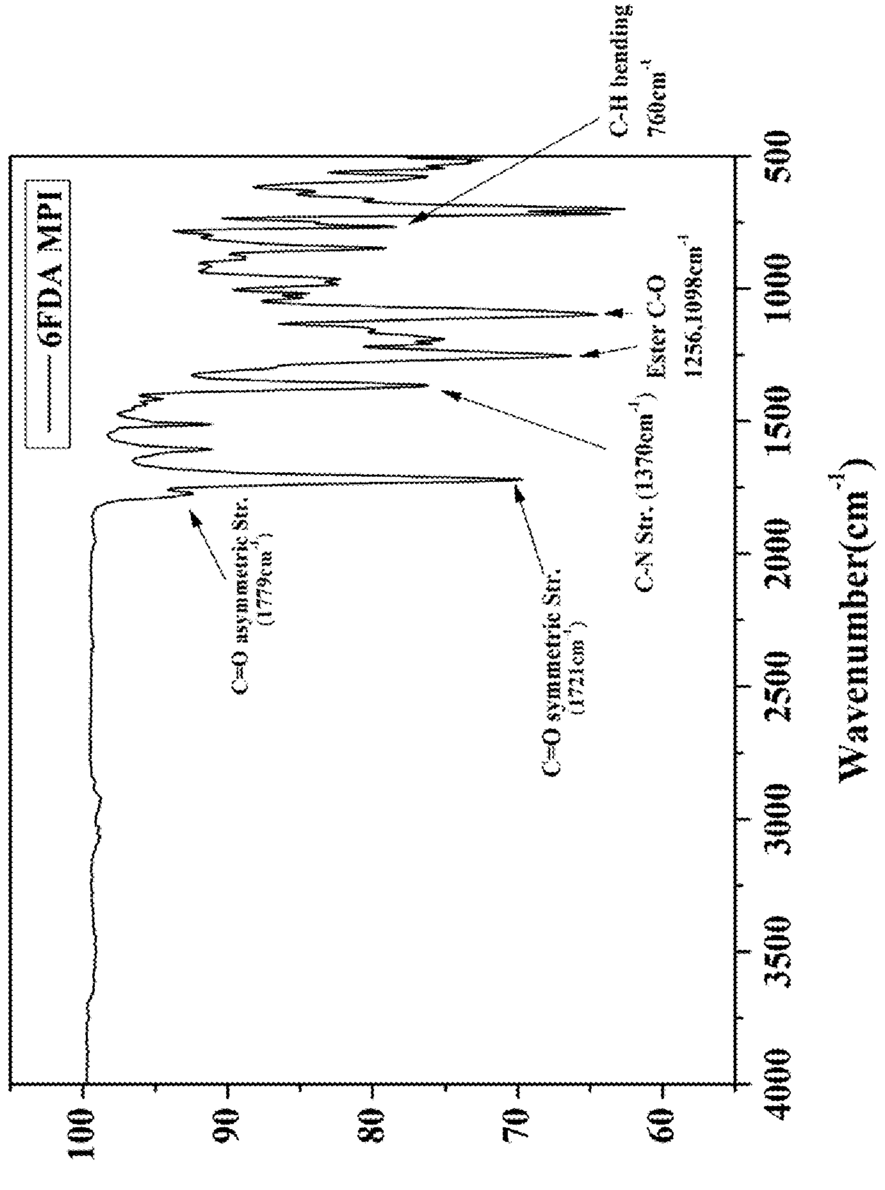
FIG. 8 shows a FT-IR spectrum of a polyimide film manufactured using 6-FDA and a novel diamine compound synthesized according to an embodiment of the present disclosure.

FIG. 8 is the FT-IR spectrum of the polyimide film manufactured according to the present disclosure. Referring to FIG. 8, a peak indicating the imide group appears at 1721 $cm^{-1}$, and a characteristic peak indicating a pentagonal ring appears at 1779 $cm^{-1}$, peaks related to the ester group appear at 1256 and 1098 $cm^{-1}$, and the peak at 1370 $cm^{-1}$ is due to the C—N—C bond of the imide group.

Experimental Example 3

Figure 9:
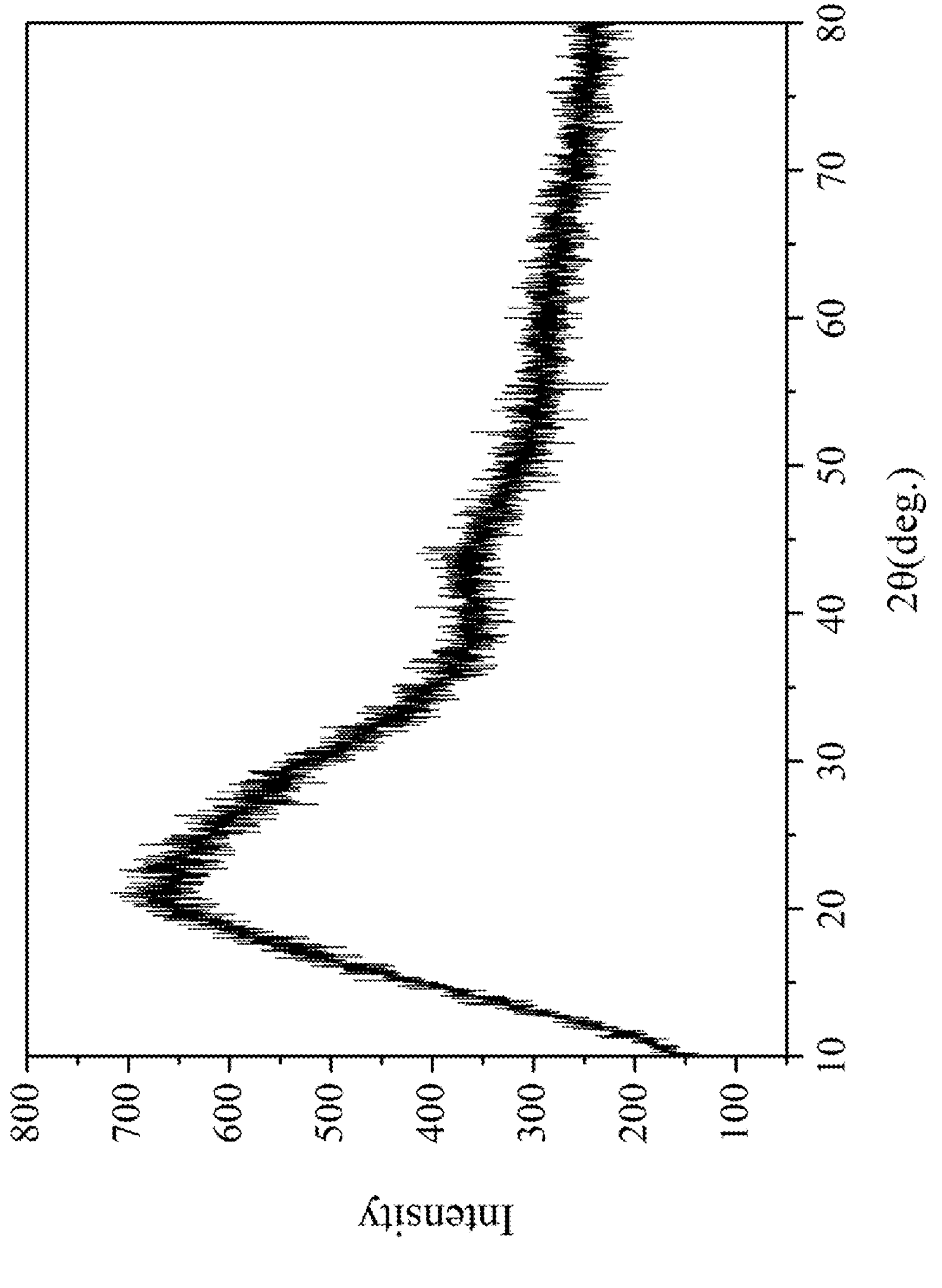
FIG. 9 shows an XRD pattern of a polyimide film according to an embodiment of the present disclosure.

The X-ray diffraction pattern of the polyimide film manufactured in accordance with the present disclosure is measured (X-ray diffraction analysis) and the results are shown in FIG. 9. Based on the results, it may be identified that as there are no specific peaks in the X-ray diffraction pattern, the manufactured polyimide film is amorphous.

Experimental Example 4

Solubility Analysis (Solubility Test)

mer main chain, thereby increasing the free volume between polymer chains such that the solvent molecule can easily penetrate into the space between molecules, and thus the polyimide powder produced in accordance with the present disclosure exhibits excellent solubility in a larger number of types of solvents than conventional polyimide does.

Furthermore, in the polyimide produced in accordance with the present disclosure, due to introduction of the bulky group, a chain packing density between polymer chains is lowered, and the flexibility of the polymer increases. When an ester moiety is introduced to the polyimide (PI) backbone, this may disrupt the CTC between the dianhydride and diamine moieties and reduce intermolecular interactions. Therefore, it may be identified that this increases the flexibility of the polymer chain and chain segment mobility and reduces the chain packing density, such that the polyimide produced in accordance with the present disclosure exhibits excellent solubility in a larger number of types of solvents than conventional polyimide does.

In one example, when 6-FDA is used as a counter dianhydride containing a —$CF_3$ group, the bulky —$CF_3$ increases the interchain space and hinders chain packing, and the low polarizability of the C—F group reduces the intermolecular force, thereby increasing the solubility.

In other words, the polyimide produced using the diamine compound according to the present disclosure exhibits high solubility because the solvent molecule can easily penetrate the polymer matrix. Further, polymerization thereof with 6-FDA may also increase the solubility thereof.

TABLE 1

| Solvent | | | | | | | | | | |
|---|---|---|---|---|---|---|---|---|---|---|
| DMSO | DMAc | DMF | NMP | THF | $CHCl_3$ | $CH_2Cl_2$ | Ethyl acetate | γ-butyrolactone | Ethanol | Methanol |
| ++ | ++ | ++ | ++ | ++ | ++ | ++ | ++ | + | − | − |

(++ means that 70% or greater of the polyimide powder is dissolved in 1 minute at room temperature (high solubility), + means that 70% or greater of the polyimide powder is dissolved in 1 minute or greater at room temperature (the polyimide powder can be dissolved, but it takes a lot of time), − means that the polyimide powder is not dissolved at room temperature)

Table 1 above shows the results of analyzing the solubility of the polyimide powder produced in accordance with the present disclosure. In this regard, 10 mg of the polyimide powder and 1 ml of each of the solvents was inputted to a test tube, and then the solubility thereof was observed.

Referring to Table 1, the produced polyimide powder exhibited excellent solubility not only in a polar solvent with a high boiling point such as dimethyl sulfoxide (DMSO) and dimethylacetamide (DMAc), but also in a polar solvent with a low boiling point such as tetrahydrofuran (THF), chloroform ($CHCl_3$), and dichloromethane ($CH_2Cl_2$) at room temperature. Furthermore, the produced polyimide powder exhibited excellent solubility in ethyl acetate.

The produced polyimide powder can be dissolved in γ-butylrolactone, but it took a time. The produced polyimide powder is insoluble in alcohol solvents such as ethanol or methanol.

Based on these results, it may be identified that in the polyimide powder produced in accordance with the present disclosure, a bulky phenyl group is introduced to the poly-

Experimental Example 5

Moisture Content and Water Contact Angle

The moisture absorption of the polyimide film manufactured in accordance with the present disclosure were measured using a method performed by M. Hasegawa's research team. A 0.1 g polyimide film was dried in a vacuum oven at 50° C. for 24 hours, then immersed in distilled water at 23° C. for 24 hours, and then the moisture was removed therefrom, and a weight thereof was measured. An equation for calculating the moisture absorption percentage is as follows.

$$W_A = [(W - W_0)/W_0] \times 100 \quad \text{[Equation]}$$

(In the above equation, $W_0$ is the weight of the polyimide film after drying the film in a vacuum oven at 50° C., and W is the weight of the polyimide film after immersion thereof in the distilled water for 24 hours.)

Figure 10:
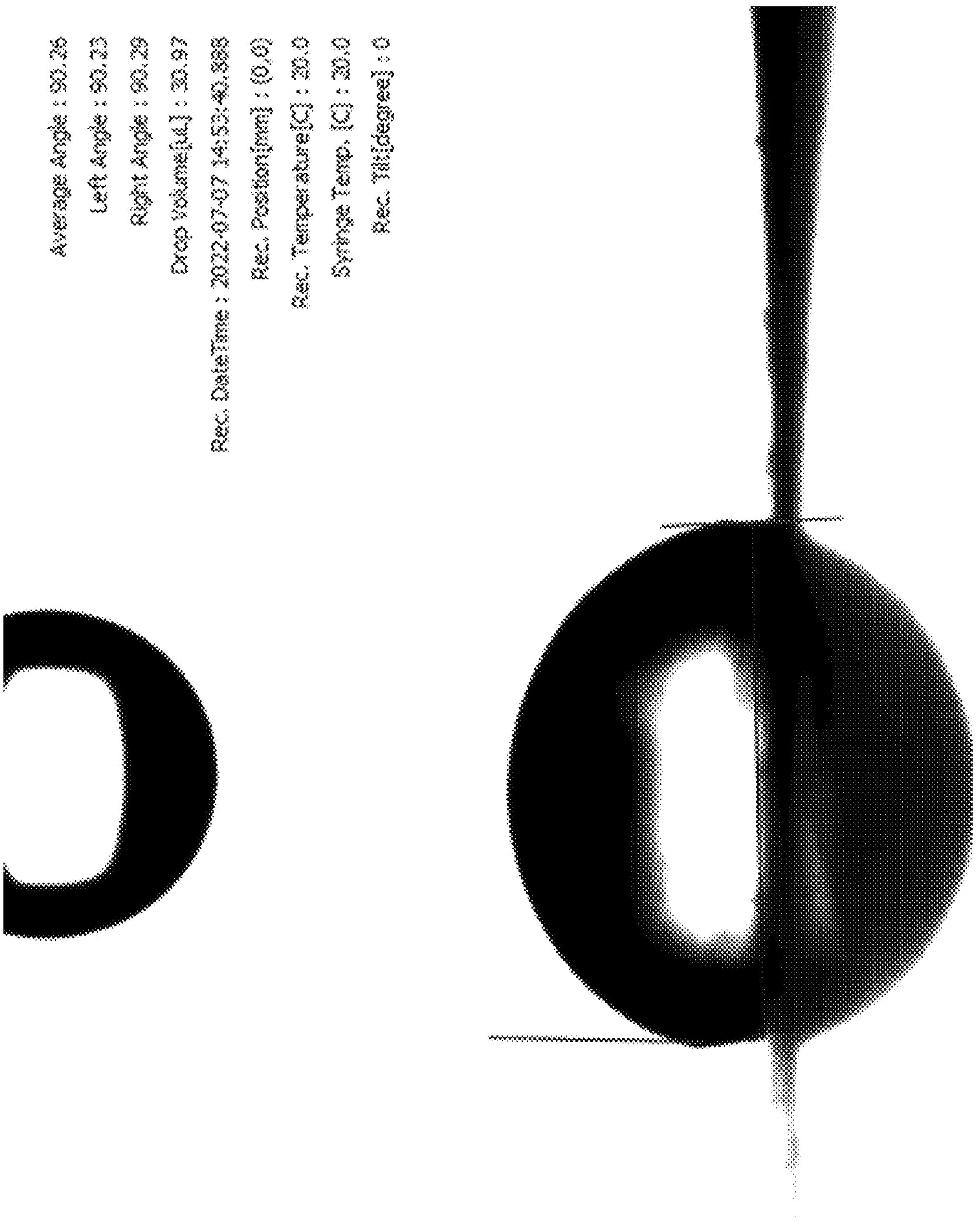
FIG. 10 shows a photograph of a water contact angle of a polyimide film according to an embodiment of the present disclosure.

As a result of the measurement, the $W_0$ of the film in accordance with the present disclosure was calculated to be 0.1067 g, and W thereof was calculated to be 0.1086 g, and thus, the moisture absorption percentage was calculated to be 1.78%. Furthermore, FIG. 10 is a photograph of a water contact angle of the produced polyimide film. Referring to FIG. 10, an average water contact angle thereof is 90.26°, indicating that the polyimide film is hydrophobic.

Thus, the polyimide film manufactured in accordance with the present disclosure may have hydrophobicity and a low moisture absorption percentage. In other words, in the polyimide film in accordance with the present disclosure, the bulky phenyl group is introduced to the polymer chain, thereby increasing the space between the polymer chains, making it easier for the moisture to penetrate therein, and at the same time, the polyimide film may maintain high solubility and at the same time, have the hydrophobicity and the low moisture absorption percentage, due to the hydrophobicity of the phenyl group and the hydrophobicity of the imide group.

Experimental Example 6

Ultraviolet and Visible Light Transparency (UV-Visble Spectrophotometer)

The ultraviolet and visible light transparency of each of the polyimide film manufactured in accordance with the present disclosure and the polyimide film according to the Comparative Example was measured using ultraviolet-visible spectrophotometry in the wavelength range of 200 to 800 nm.

TABLE 2

| PI | $T_{vis}$ (%) | $T_{450}$ (%) | $T_{400}$ (%) | $\lambda_{cutoff}$ (nm) | $\Delta\varepsilon$(eV) | Film thickness (μm) |
|---|---|---|---|---|---|---|
| 6FDA-DPEDBA | 87.1 | 85.57 | 51.1 | 365 | ~3.2 | 40 |
| PMDA-ODA | 55.0 | 0.29 | 0.18 | 465 | ~2.45 | 38 |

Figure 11:
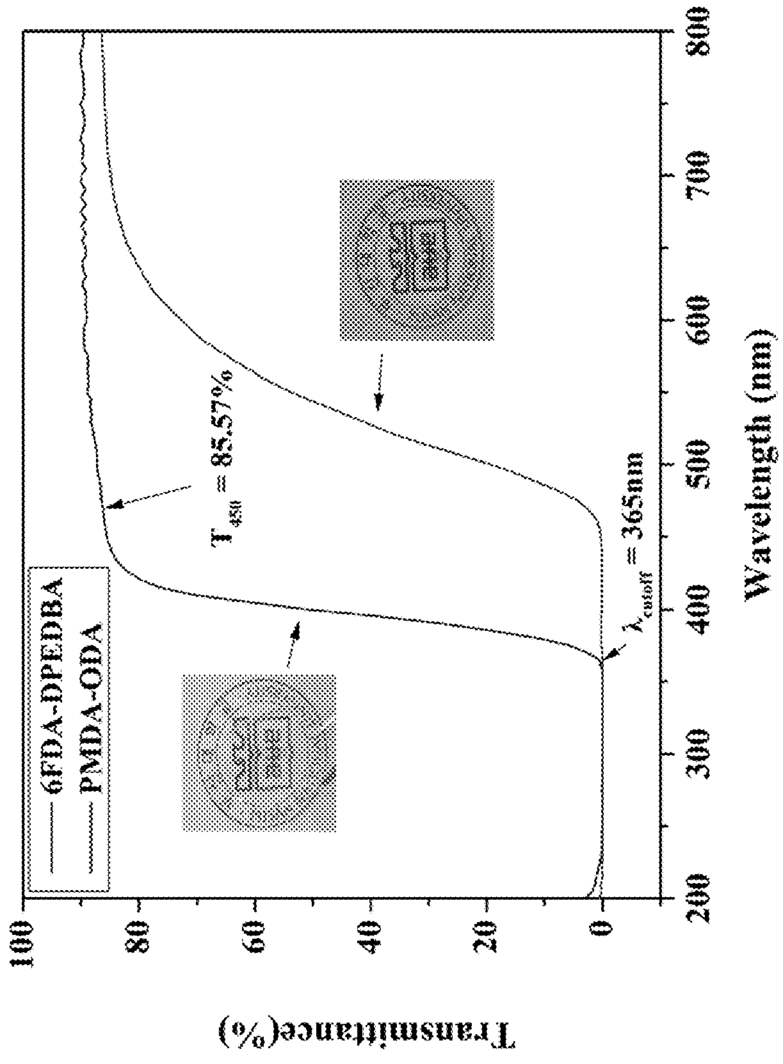
FIG. 11 shows an ultraviolet-visible spectrum and a light transmission image of a polyimide film according to each of Present Example and Comparative Examples of the present disclosure.

Referring to Table 2 and FIG. 11 showing the results, the average transmittance of light in the visible light region (400 to 760 nm) of the polyimide film in accordance with the present disclosure is 87.1%, and the transmittance thereof at 450 nm is 85.57%, indicating that the polyimide film in accordance with the present disclosure exhibits excellent colorless transparency. This is because the coloring effect caused by the charge transfer complex unique to the polyimide is successfully suppressed. Specifically, the ester group and the bulky phenyl group introduced into the novel diamine monomer effectively increases the free volume between polyimide polymer chains and suppresses the charge transfer complex acting between the polyimide polymer chains. These results imply that the polyimide film in accordance with the present disclosure may be converted to a transparent substrate.

On the contrary, a PMDA-ODA polyimide film according to the Comparative Example exhibits a yellow-dark brown color due to the chemical structure of the PI main chain. This is due to coloration due to intra-molecular and inter-molecular CTCs between the electron-accepting dianhydride and the electron-donating diamine. Based on a result of calculating the band gap ($\Delta\varepsilon$) between the HOMO energy and the LUMO energy, the polyimide film according to the Comparative Example exhibits a smaller band gap difference, thus indicating that in the polyimide film according to the present disclosure, the strong interaction due to the bonding effect between the polymer chains according to the molecular structure is effectively reduced.

Experimental Example 7

Thermal Properties

Figure 12:
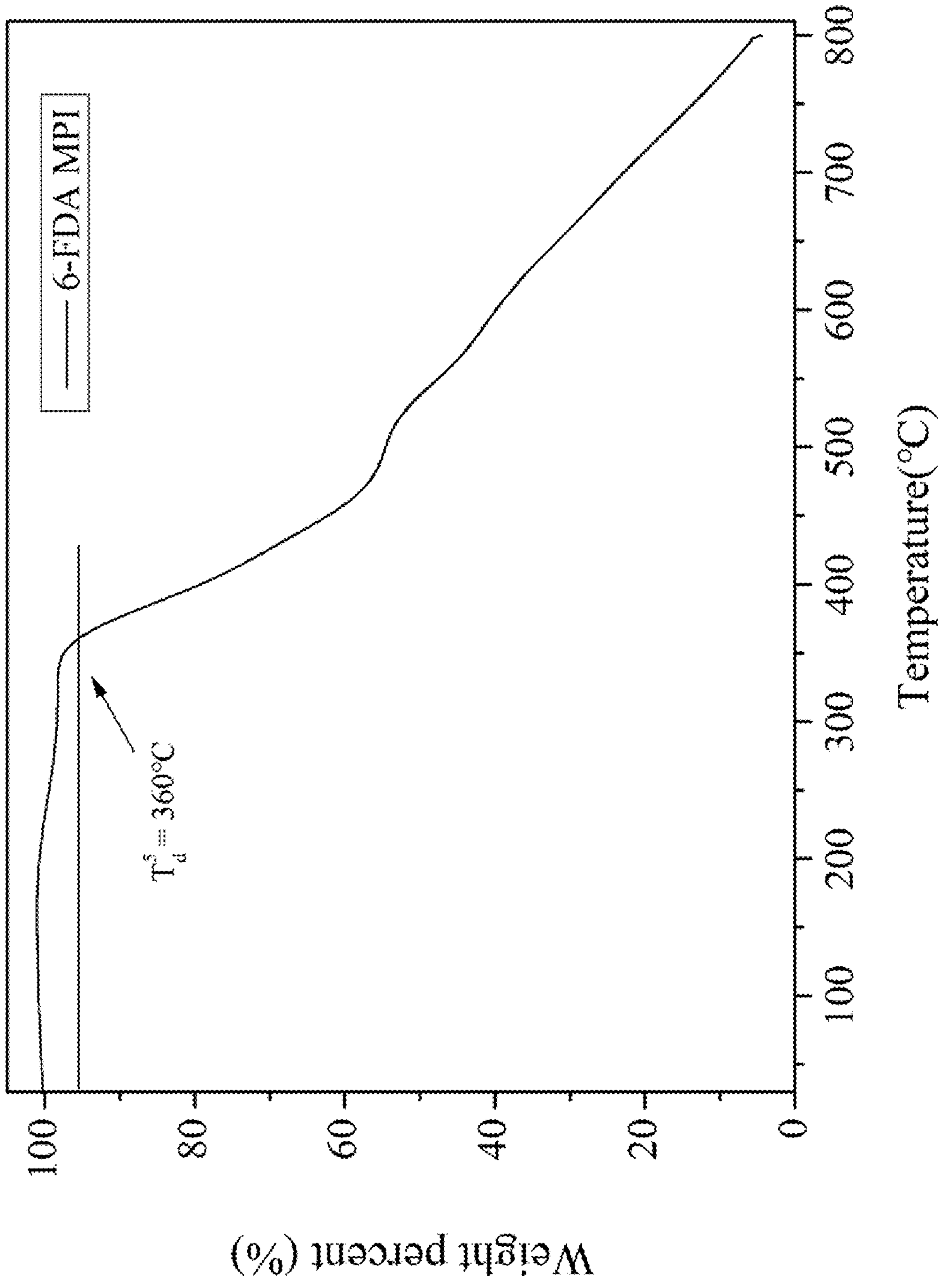
FIG. 12 shows a thermogravimetric analysis curve of a polyimide film according to an embodiment of the present disclosure.

A thermal property test was measured via TGA. The TGA curve in FIG. 12 shows the thermal stability of the polyimide film manufactured in the present disclosure. Referring to FIG. 12, the 5 weight percent loss temperature ($Td^5$) was found to be 360° C. Despite the introduction of the phenyl group connected to the ester group via a single bond to the novel diamine monomer, the polyimide film manufactured in the present disclosure exhibits thermal stability at temperatures above 350° C.

Experimental Example 8

Molecular Weight Analysis

Figure 13:
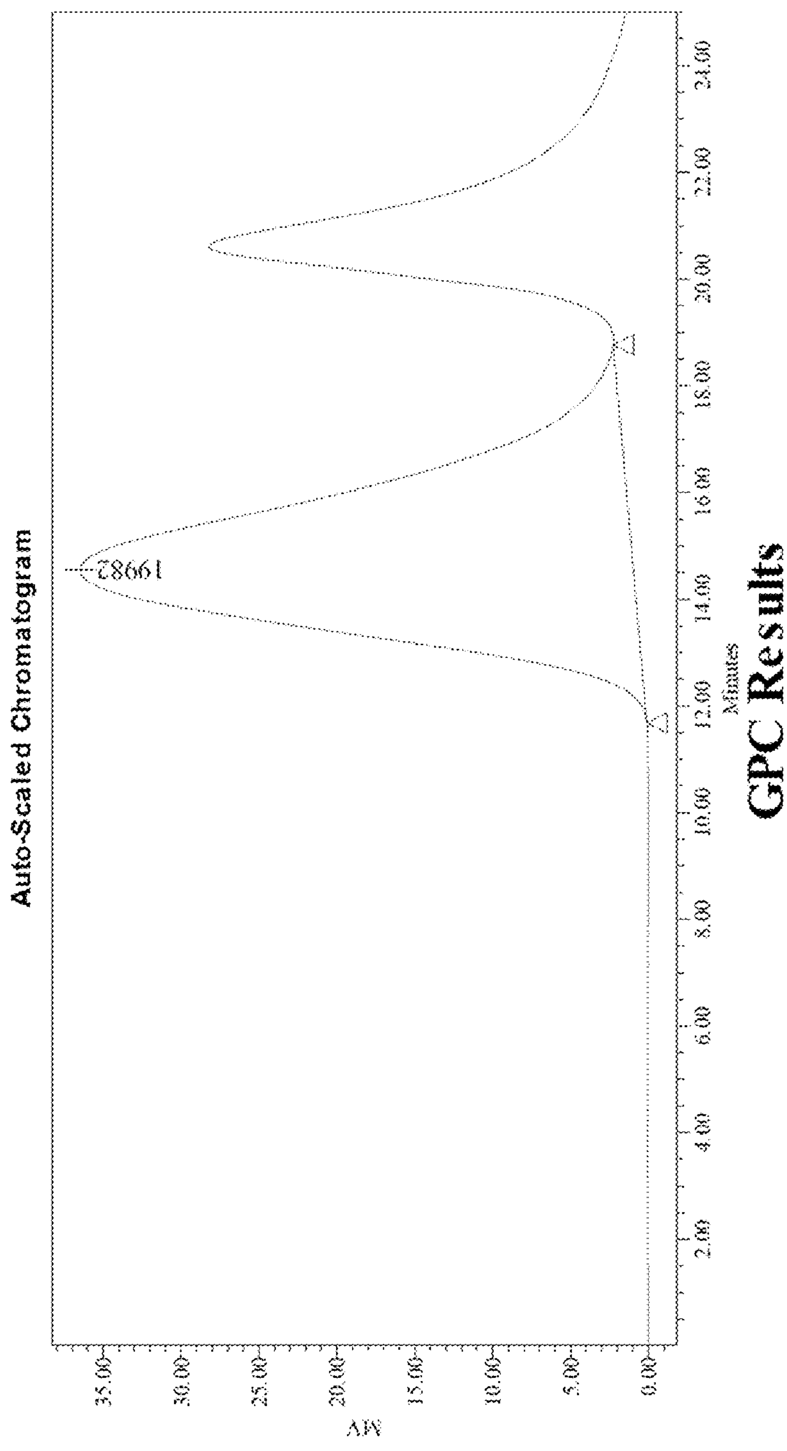
FIG. 13 shows a GPC graph and an average molecular weight analysis result of polyimide according to an embodiment of the present disclosure.

FIG. 13 is a graph showing the molecular weight of the polyimide polymer produced in the present disclosure. The molecular weight of the polyimide polymer was measured by gel permeation chromatography (GPC) using tetrahydrofuran and polystyrene as a solvent and a standard, respectively. The number average molecular weight (Mn) and the weight average molecular weight (Mw) of the polyimide polymer produced in accordance with the present disclosure are 10600 and 23300, respectively, indicating that the newly developed diamine monomer reacts with dianhydride to successfully produce the polymer.

Experimental Example 9

Dielectric Properties

Figure 14:
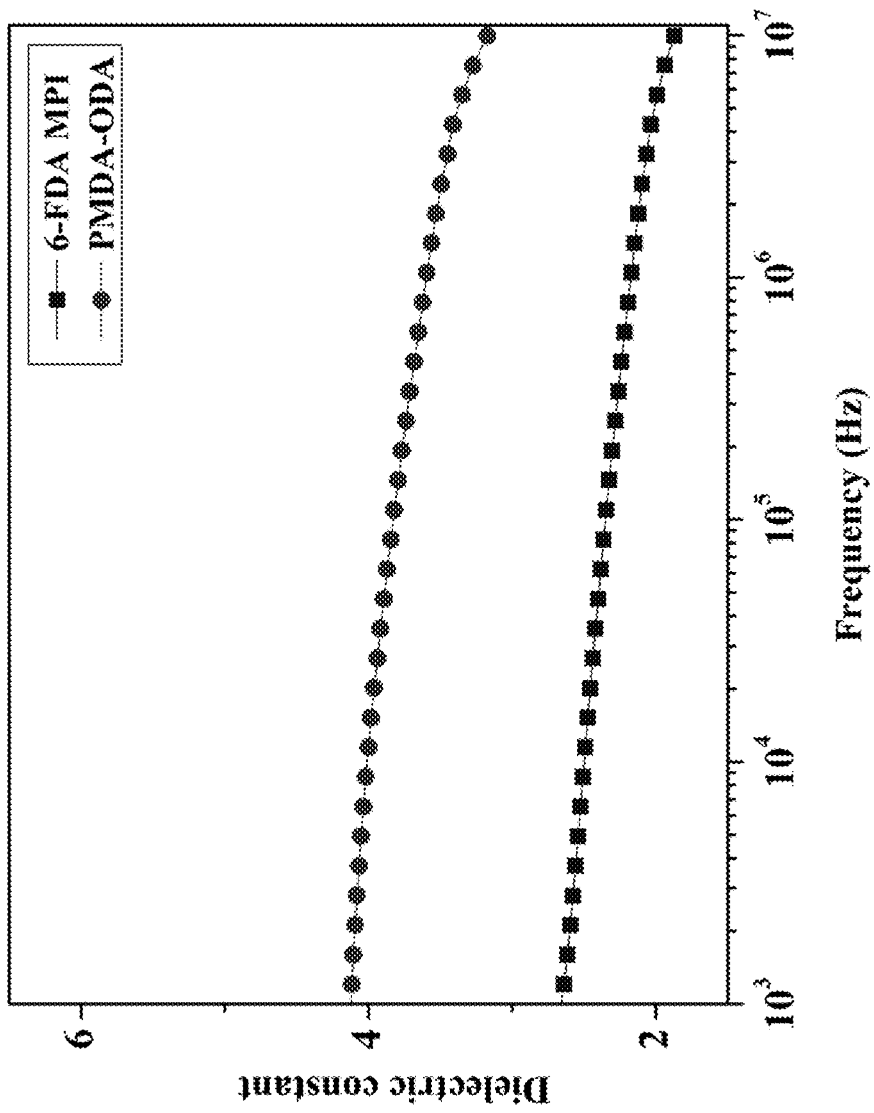
FIG. 14 shows a dielectric constant graph of a polyimide film according to each of Present Example and Comparative embodiment of the present disclosure.

The dielectric properties of each of the polyimide film manufactured in accordance with the present disclosure and the polyimide film according to the Comparative Example was measured in a range from $10^3$ Hz to $10^7$ Hz, and the results are shown in FIG. 14. The dielectric constant of the polyimide film according to the present disclosure (blue line) exhibits a very low dielectric constant of 2.17 at 1 MHz, while the dielectric constant of the PMDA-ODA polyimide film according to the Comparative Example (red line) exhibits a high dielectric constant of 3.59 at 1 MHz. This is because due to the ester group and the bulky phenyl group contained in the novel diamine monomer, an imide group content (Imide %) in the main chain of the polyimide polymer chain is reduced, and the space between the polymer chains is expanded, thereby suppressing the charge transfer complex. Furthermore, when 6-FDA is selected as dianhydride, a fluorine content (F %) in the polymer chain increases, thereby effectively lowering the dielectric constant.

In one example, the polyimide film in accordance with the present disclosure exhibits a dielectric constant of 1.87 at $10^7$ Hz. The dielectric constant thereof tends to decrease as the frequency increases.

Summarizing the above results, the polyimide film according to the present disclosure is colorless and transparent, has the low moisture absorption percentage and the low dielectric properties, and thus, may be usefully used in the next generation communication industry and electronic device substrates.

Although the embodiments of the present disclosure have been described in more detail with reference to the accompanying drawings, the present disclosure is not necessarily limited to these embodiments, and may be modified in a various manner within the scope of the technical spirit of the present disclosure. Accordingly, the embodiments as disclosed in the present disclosure are intended to describe rather than limit the technical idea of the present disclosure, and the scope of the technical idea of the present disclosure is not limited by these embodiments. Therefore, it should be understood that the embodiments described above are not restrictive but illustrative in all respects.

What is claimed is:

1. A diamine compound represented by a following Chemical Formula 1:

[Chemical Formula 1]

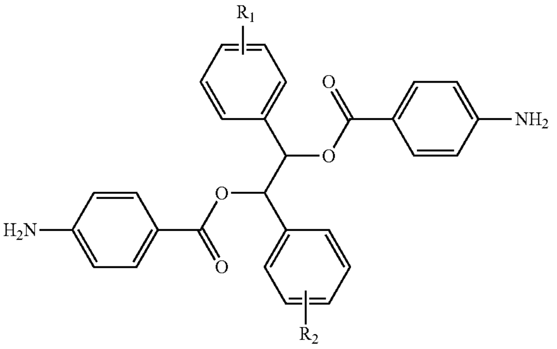

where in the Chemical Formula 1, each of $R_1$ and $R_2$ independently represents hydrogen, an alkyl group having 1 to 5 carbon atoms, or a trifluoromethyl group.

2. The diamine compound of claim 1, wherein the diamine compound is represented by a following Chemical Formula 1-1:

[Chemical Formula 1-1]

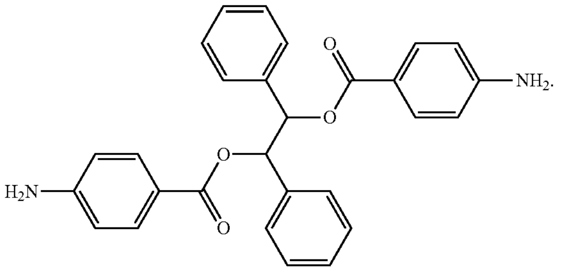

3. A polyimide precursor produced by polymerizing of a polymerization component containing at least one acid dianhydride and the diamine compound according to claim 1.

4. The polyimide precursor of claim 3, wherein the acid dianhydride is 6-FDA (4,4'-(hexafluoroisopropylidene)diphthalic anhydride).

5. Polyimide produced from the polyimide precursor according to claim 3.

6. The polyimide of claim 5, wherein the polyimide is represented by a following Chemical Formula 2:

[Chemical Formula 2]

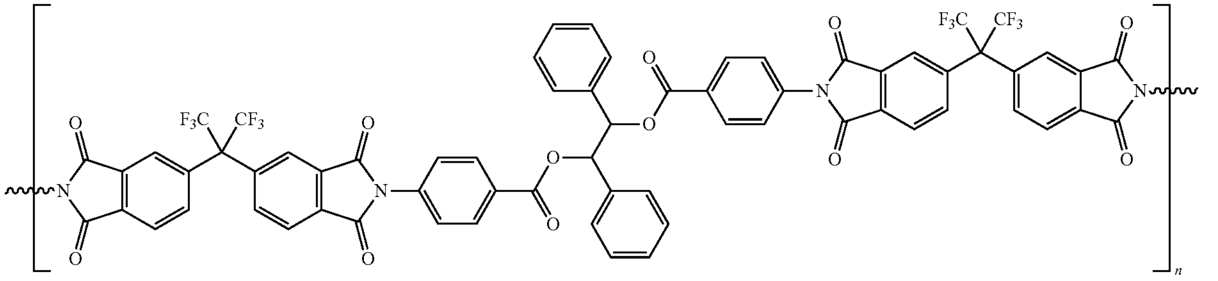

where in the Chemical Formula 2, n is an integer from 8 to 75.

7. The polyimide of claim 6, wherein the polyimide is soluble in a polar solvent selected from a group consisting of dimethyl sulfoxide (DMSO), dimethylacetamide (DMAc), tetrahydrofuran (THF), chloroform ($CHCl_3$), dichloromethane ($CH_2Cl_2$), ethyl acetate, and γ-butylrolactone at a temperature of 10 to 40° C.

8. The polyimide of claim 6, wherein a weight average molecular weight (Mw) of the polyimide is in a range of 20,000 to 25,000.

9. A polyimide film manufactured by dissolving the polyimide according to claim 6 in a polar solvent at a temperature of 10 to 40° C. to produce a solution, and applying the produced solution on a substrate, and then drying the applied solution, wherein the polar solvent is selected from a group consisting of dimethyl sulfoxide (DMSO), dimethylacetamide (DMAc), tetrahydrofuran (THF), chloroform ($CHCl_3$), dichloromethane ($CH_2Cl_2$), ethyl acetate, and γ-butylrolactone.

* * * * *